(12) United States Patent
Kolter et al.

(10) Patent No.: US 8,268,350 B2
(45) Date of Patent: Sep. 18, 2012

(54) BINDERS FOR TABLETS WITH HIGH STRENGTH BASED ON FINELY DIVIDED VINYLLACTAM POLYMERS, THE PRODUCTION AND USE THEREOF

(75) Inventors: Karl Kolter, Limburgerhof (DE); Hermann Ascherl, Dirmstein (DE); Bernhard Fussnegger, Kirrweiler (DE)

(73) Assignee: BASF SE, Ludwigshafen (DE)

( * ) Notice: Subject to any disclaimer, the term of this patent is extended or adjusted under 35 U.S.C. 154(b) by 782 days.

(21) Appl. No.: 11/406,320

(22) Filed: Apr. 19, 2006

(65) Prior Publication Data
US 2006/0240102 A1 Oct. 26, 2006

(30) Foreign Application Priority Data
Apr. 20, 2005 (DE) .......................... 10 2005 018 465

(51) Int. Cl.
*A61K 9/20* (2006.01)
(52) U.S. Cl. ...................................... 424/464
(58) Field of Classification Search ........................ None
See application file for complete search history.

(56) References Cited

U.S. PATENT DOCUMENTS

| | | | |
|---|---|---|---|
| 5,176,713 A * | 1/1993 | Dixit et al. ...................... 8/137 |
| 5,426,163 A | 6/1995 | Buehler et al. |
| 5,674,436 A | 10/1997 | Breitenbach et al. |
| 6,829,843 B2 | 12/2004 | Fujise et al. |
| 2003/0108616 A1* | 6/2003 | Bosch et al. ................. 424/497 |
| 2004/0139625 A1 | 7/2004 | Fujise |
| 2005/0019412 A1* | 1/2005 | Bosch et al. ................. 424/489 |

FOREIGN PATENT DOCUMENTS

| | | |
|---|---|---|
| CA | 2151770 | 12/1995 |
| DE | 0 545 209 A1 | 6/1993 |
| EP | 0 437 375 B1 | 7/1991 |
| EP | 0687694 A2 | 12/1995 |
| EP | 0 714 919 A2 | 6/1996 |
| EP | 0715848 A2 | 6/1996 |
| EP | 1437375 A1 | 7/2004 |

OTHER PUBLICATIONS

Kollidon® VA 64 leaflet (Published by BASF, Mar. 2000).*
Vgl. V. Buhler, 2005 "Polyvinylpyrrolidone Excipients for Pharmaceuticals", S. 18-20 and 186-188, Springer-Verlag Berlin Heidelberg.

* cited by examiner

*Primary Examiner* — Paul Dickinson
(74) *Attorney, Agent, or Firm* — Connolly Bove Lodge & Hutz LLP

(57) ABSTRACT

Finely divided binders in powder form composed of vinyl-lactam polymers, where the binders have an average particle size of up to 35 μm and an apparent density of less than 0.2 g/ml.

3 Claims, 1 Drawing Sheet

I
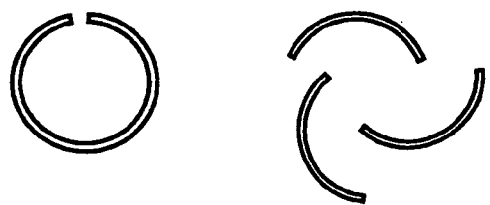
II
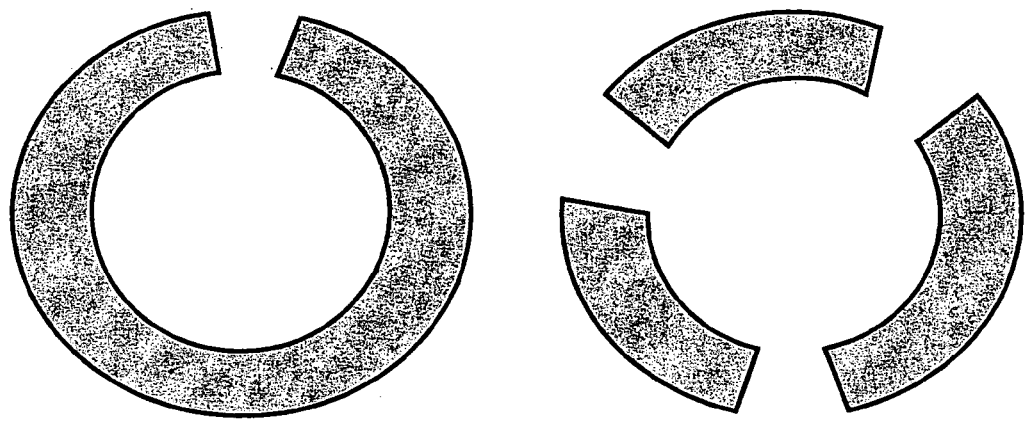
III
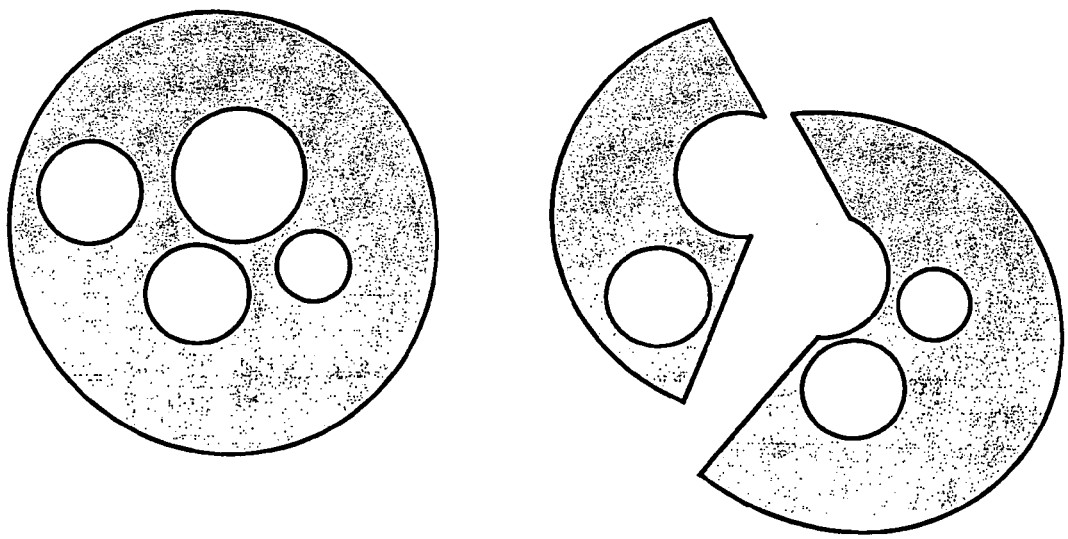

BINDERS FOR TABLETS WITH HIGH STRENGTH BASED ON FINELY DIVIDED VINYLLACTAM POLYMERS, THE PRODUCTION AND USE THEREOF

CROSS REFERENCE TO RELATED APPLICATION

The present application claims priority from German Patent Application No. 10 2005 018 465.0, filed Apr. 20, 2005.

The present invention relates to binders based on finely divided vinyllactam polymers in powder form, where the binders have an average particle size of up to 35 µm and an apparent density of up to 0.2 g/ml. The binders are preferably in the form of hollow spheres or parts of such hollow spheres having a wall thickness of <3 µm, where the ratio of the diameter to the wall thickness is >10. The invention further relates to a process for producing such binder particles and to the use thereof for producing tablets with high strength.

Binders are ordinarily employed in the production of compressed dosage forms in order to improve the resistance to crushing and the friability. Two tablet production processes normally exist: wet granulation and direct tableting. Binders can be classified according to these applications into wet binders and dry binders. Application of dry binders takes place, as the name suggests, in dry form, that is no dissolving in a solvent takes place. Direct tableting is naturally the more costeffective process because the individual components need merely to be mixed, but developments frequently fail because an efficient dry binder is not available. Medicinal substances and also many other substances employed in tablets frequently have poor tableting properties, attributable in particular to the impossibility of generating any bonding between the solid particles of these materials during compression, or the materials being so elastic that the bonding is disrupted again on elastic relaxation. It would naturally be possible in principle to compensate this by a high proportion of binder in the tablet. However, this is not expedient because the mass and the volume of the tablet are increased thereby, and it can then scarcely be swallowed. In addition, high proportions of binder prolong the disintegration time and dissolution of the active ingredient. Many medicinal substances therefore cannot be formulated by direct tableting.

The effect of dry binders is also important in roll compaction because it is necessary in this case too for a strong cohesion between the particles of the tablet ingredients to be generated. If this is not the case, the result of the roll compaction is mechanically unstable and disintegrates on comminution again virtually to the initial particle size, flows poorly and provides inadequate resistance to crushing and friability in the subsequent tableting.

At present, no dry binder with adequate binder properties for solving these problems is available.

Examples of frequently used conventional binders are vinyllactam polymers. Vinyllactam polymers are commercially available and are marketed for example under the names Kollidon® (BASF Aktiengesellschaft) and Plasdone® (International Speciality Products Inc.). The average particle size of these products is in the range from 50 to 250 µm. The particles have a thick-walled or irregular structure and have relatively high apparent densities (cf. V. Bühler in "Polyvinylpyrrolidone Excipients for Pharmaceuticals", pp. 18-20 and 186-188, Springer-Verlag Berlin Heidelberg, 2005).

EP-A 545209 discloses the preparation of water-insoluble vinylpyrrolidone/vinyl acetate copolymers in powder form, which are obtained by atomizing aqueous dispersions.

EP-A 714 919 discloses the preparation of polyvinylpyrrolidone/hydrogen peroxide complexes in powder form by spray drying, where the spray drying takes place with relatively low pressures.

EP-A 1 437 375 discloses vinylpyrrolidone polymers in powder form with high apparent density, which are obtained by atomization with the aid of a rotating disk.

It was an object of the present invention to find a binder based on polyvinyllactams with improved binder properties for producing very stable tablets.

We have found that this is achieved by binders based on finely divided vinyllactam polymers in powder form which have average particle sizes of from 1 to 35 µm.

These binders are preferably in the form of hollow spheres or parts of such hollow spheres, where the wall thickness of the hollow spheres is less than 3 µm and the ratio of the diameter of the hollow spheres to the wall thickness is greater than 10:1.

The method used for determining the average particle size is the $D(4,3)$ value derived from diffraction of light. This particle size should be less than 35 µm, preferably less than 30 µm and particularly preferably less than 20 µm, with a lower limit for the average particle size of 2 µm.

The wall thickness of the hollow spheres or of the parts or fragments thereof should preferably be less than 3.0 µm, in particular less than 2.5 µm and particularly preferably less than 2.0 µm, with a lower limit of 0.05 µm, and the ratio of the diameter of the hollow sphere to the shell thickness should be greater than 10:1, preferably greater than 12:1 and particularly preferably greater than 15:1.

The apparent density is usually less than 0.2 g/ml, in particular from 0.05 to 0.18 g/ml. The apparent density is determined according to Pharm. Eur. 2.9.15.

The BET surface area is usually above 1 $m^2$ per gram and may be up to 50 $m^2/g$.

Reference to polyvinyllactams according to the invention means water-soluble homopolymers, copolymers, terpolymers, block copolymers or graft copolymers. These polymers may comprise N-vinylpyrrolidone or N-vinylcaprolactam or mixtures thereof as the following monomers having a lactam structure.

Suitable further comonomers are the vinyl esters of saturated $C_1$-$C_{20}$-carboxylic acids such as, for example: vinyl acetate, vinyl propionate, vinyl laurate, vinyl stearate.

Water-soluble copolymers of vinylpyrrolidone and vinyl acetate are particularly preferred and ratios of vinylpyrrolidone to vinyl acetate of from 60:40 to 80:20 are very particularly preferred, in particular copolymers of N-vinylpyrrolidone and vinyl acetate in the ratio of 6:4 by weight, K value 25-30.

Homopolymers of N-vinylpyrrolidone are additionally preferred.

The Fikentscher K values, a measure of the molecular weight of the polymers, may be from 10 to 120, preferably 12 to 90, particularly preferably 15 to 60.

Binders preferred according to the invention are those consisting of 100% by weight polyvinyllactam polymers. However, further substances may be added if desired.

Thus, plasticizing substances may be added to improve the plasticity of the binders. Plasticizing substances which can be employed are typical plasticizers such as triethyl citrate, triacetin, propylene glycol, glycerol, polyethylene glycol and similar known substances. The proportion of these substances in the binder of the invention is from 0 to 20% by weight, preferably less than 10% by weight.

The binders of the invention may additionally comprise, besides the vinyllactam polymer, also surface-active substances. Surface-active substances are substances which reduce the interfacial tension at an interface. The surface-active substances employed according to the invention are surfactants, especially surfactants having an HLB (HLB=hydrophilic-lipophilic balance) above 10. A list of suitable substances is to be found in Fiedler, Lexikon der Hilfsstoffe, Editio Cantor Verlag Aulendorf, 5th edition, pages 117-121. Examples of suitable surfactants are salts of fatty acids such as, for example, sodium dodecylate, sodium stearate, sodium oleate or sodium palmitate, and salts of alkyl sulfates such as, for example, sodium lauryl sulfate. Also suitable are polyethoxylated sorbitan fatty acid esters such as polysorbate 20 or ethoxylated 12-hydroxystearic acid or polyglycerol fatty acid esters. Ethoxylated derivatives of castor oil or hydrogenated castor oil are also suitable, for example products of the reaction of 35 mol of ethylene oxide with castor oil or of 40 ml of ethylene oxide with hydrogenated castor oil. Such surfactants can be employed in amounts of from 0 to 20% by weight, preferably up to 10% by weight.

Spray-drying processes are suitable for producing the products of the invention, and entail a solution of the vinyllactam polymers being finely atomized with the aid of nozzles and then dried in a stream of hot air. Aqueous solutions are preferably processed.

It is possible to use single fluid nozzles or multifluid nozzles for the atomization. Particularly suitable multifluid nozzles are dual fluid nozzles. It is crucial that small droplets are achieved and the dried particles do not stick together.

The atomization takes place at high pressure for the particular type of nozzle. On atomization through single fluid nozzles, nozzle diameters of from 0.1 to 3 mm have proved suitable, preferably 0.2 to 1 mm, particularly preferably 0.4 to 0.8 mm, and pressures above 8 MPa have proved particularly suitable, preferably greater than 12 MPa, very particularly preferably greater than 16 MPa. The atomization pressure in the case of the single fluid nozzle can be up to 25 MPa. On atomization through dual fluid nozzles, nozzle diameters (liquid side) of from 0.6 to 10 mm have proved suitable, preferably 0.8 to 3 mm, particularly preferably 1 to 3 mm, and pressures of the atomizing gas above 0.2 MPa have proved suitable, particularly preferably above 0.4 MPa, very particularly preferably above 0.6 MPa. The pressure of the atomizing gas can be up to 1 MPa. Suitable atomizing gases are the same gases as employed for drying.

The solids concentrations of the solutions to be atomized are between 1 and 35% by weight, preferably between 3 and 25% by weight and particularly preferably between 5 and 15% by weight.

In a preferred embodiment, the spray solution is preheated to temperatures of 40-180° C.

The atomization can take place in any spray tower of conventional design. Drying gases which can be used are air or inert gases such as nitrogen, argon or helium, which can be passed through the drying tower cocurrently or countercurrently to the liquid droplets. The drying gas is preferably employed cocurrently. The tower inlet temperature of the drying gas is from 80 to 250, preferably 100 to 200, ° C. The tower outlet temperature is from 40 to 130, preferably 50 to 110, ° C.

Vaporization of the solvent can take place both under atmospheric pressure and under slightly elevated or reduced pressure (+/−0.01 MPa). The resulting powder can be removed from the gas stream for example via a cyclone or a filter.

It has surprisingly been found that binders based on vinyllactam polymers having a particular shape of the particles have greatly improved binder activities.

The FIGURE depicts diagrammatically particles (I) of the invention and prior art particles (commercially available products; II: Kollidon VA 64; III: Plasdone S 630).

In order to reduce the particle size of the binders of the invention further if desired before processing, it is possible for products sprayed in this way to be ground using conventional mills such as, for example, air jet mills, pinned-disk mills. It is possible by grinding to adjust the average particle size for example to values of from 1 to 20 μm.

The products of the invention are ordinarily used by mixing with the other ingredients of the formulation and subsequently compressing to a tablet or a compact. The decisive point in this connection is that the dry binder is uniformly distributed in the mixture. In a particular embodiment, it is also possible after the mixing to add water, steam or an organic solvent, thus partly dissolving the small particles and leading to a high strength of the tablet or the compact.

A tablet is normally produced in a tablet press, and a compact is produced in a roll compactor. For further processing, the compact is comminuted again to granules which can be mixed with further additives and can for example be compressed to a tablet. The process of roll compaction is also referred to as dry granulation.

The compression to tablets can take place under compressive forces of up to 800 MPa.

The tablets obtained with the aid of the binders of the invention have a high strength. The strength can be from 40 to 600 N.

The proportion of the dry binder in the formulation should be 0.5-20% by weight, preferably 1-15% by weight and particularly preferably 2-12% by weight. The fact that the dry binders of the invention have enormous binding properties makes it possible also for poorly compressible active ingredients and excipients to be compressed, especially when they are also present in high concentration.

The binders of the invention themselves have relatively poor flowability because of the fine particles. Thus, the flowability resulting on mixture with other ingredients ought also to be relatively poor. However, surprisingly, in these cases the flowabilities prove to be better.

Binders are frequently tacky substances which increase the ejection force during tableting, thus possibly causing numerous problems such as, for example, reduced strength of the tablet, capping, large rise in temperature of the compression tools and of the die wall, increased wear of the press etc. Entirely unexpectedly, the binders of the invention show a lubricant effect, since the residual and ejection forces during tableting are distinctly lower than without use of a binder or with use of a conventional binder.

The preparation process and thus also the preferred hollow spherical or shell-like structure is crucial for the particular effect of the binders, which is shown as high resistance to crushing and low friability of the tablets. Thus, products produced by grinding display a considerably smaller effect of the binders at the same average particle size.

It is surprisingly possible, despite a higher mechanical strength of the tablets, to find no prolongation of the disintegration time. Overall, the disintegration time of tablets having the binders of the invention is rapid.

In summary, the binders of the invention lead to tablets with exceptional mechanical properties, they make it possible to compress medicinal substances which are compressible with difficulty or not at all, they make it possible to reduce the total tablet mass or the tablet volume, and they ensure that the tableting process proceeds without impediment.

The binders of the invention are particularly suitable for producing tablets of the following active pharmaceutical ingredients which are normally difficult to compress:

paracetamol, carbamazepine, acetylsalicylic acid, ascorbic acid, metoprolol tartrate, ibuprofen, pseudoephedrine HCl, diphenhydramine HCl, dimenhydrinate, indometacin, diclofenac sodium, N-acetylcysteine, albendazole, alpha-methyldopa, aluminum hydroxides, magnesium silicate, ampicillin, atenolol HCl, captopril, cimetidine, diltiazem, griseofulvin, levamisole, magaldratei, magnesium carbonate, mebendazole, meprobamate, metamizole, metronidazole, neomycin sulfate, oxytetracycline HCl, nitrofurantoin, nystatin, nicotinic acid, phenytoin, piroxicam, pyrazinamide, ranitidine, tetracycline, amoxicillin, chloroquin diphosphate, ethambutol, gemfibrozil, mefenamic acid, metformin HCl, nalidixic acid, naproxen, probenecid, rifampicin, sulfadiazine, sulfadimidine, sulfadoxine, sulfamethoxazole, sulfathiazole, valproic acid, verapamil, aciclovir, allopurinol, bezafibrate, carbidopa, cefuroxime, cephachlor, ciprofloxacin, fenofibrate, alpha-lipoic acid, pentoxyfylline, piracetam, propafenone HCl, roxithromycin, sotalol, sulpiride, tramadol, tilidine.

EXAMPLES

The spray dryer used was a pilot plant spraying tower from Niro, type Minor (Examples 1, 3-8, 12, 13) or a manufacturing spraying tower from Zimmerling, diameter 7 m (Example 2).

Unless indicated otherwise, percentage data refer to percentages by weight.

Example 1

A 10% strength aqueous solution of Kollidon K30, a polyvinylpyrrolidone with a K value of 30 (measured in a 1% by weight solution), was dried in a spray dryer at an inlet air temperature of 170° C. The spray solution was heated to 80° C. before the atomization, and the atomization to fine droplets took place using a single fluid nozzle (diameter 0.5 mm) with a pressure of 16 MPa. The outlet air temperature was 85° C.

A fine powder with an average particle size of 17 µm and an apparent density of 0.12 g/ml was obtained.

Examination under the microscope showed the presence of hollow spheres and fragments thereof (shells).

Example 2

A 10% strength aqueous solution of Kollidon VA 64, a copolymer of N-vinylpyrrolidone (VP) and vinyl acetate (VAc) in the ratio 6:4 by weight, K value 28 (measured as 1% by weight solution in water) was dried in a spray dryer at an inlet air temperature of 150° C. The spray solution was heated to 80° C. before the atomization, and the atomization to fine droplets took place using a single fluid nozzle (diameter 1.2 mm) with a pressure of 18 MPa. The outlet air temperature was 72° C.

A fine powder with an average particle size of 15 µm and an apparent density of 0.10 g/ml was obtained.

Examination under the microscope showed the presence of hollow spheres and fragments of hollow spheres (shells) with wall thicknesses of 1.0 µm.

Example 3

A solution of 10% Kollidon 30 (polyvinylpyrrolidone, K value 30) and 0.3% triethyl citrate in water was prepared and dried in a spray dryer at an inlet air temperature of 145° C. The spray solution was heated to 75° C. before the atomization, and the atomization to fine droplets took place using a single fluid nozzle (diameter 0.5 mm) with a pressure of 16 MPa. The outlet air temperature was 71° C.

A fine powder with an average particle size of 16 µm and an apparent density of 0.11 g/ml was obtained.

Examination under the microscope showed the presence of hollow spheres and fragments of hollow spheres (shells) with wall thicknesses of 1.2 µm.

Example 4

A solution of 10% Kollidon 30 and 0.5% polysorbate 80 in water was prepared and dried in a spray dryer at an inlet air temperature of 145° C. The spray solution was heated to 75° C. before the atomization, and the atomization to fine droplets took place using a single fluid nozzle (diameter 0.4 mm) with a pressure of 16 MPa. The outlet air temperature was 71° C.

A fine powder with an average particle size of 13 µm and an apparent density of 0.11 g/ml was obtained.

Examination under the microscope showed the presence of hollow spheres and fragments of hollow spheres (shells) with wall thicknesses of 0.9 µm.

Example 5

A solution of 5% Kollidon VA 64 and 0.1% sodium lauryl sulfate in water was prepared and dried in a spray dryer at an inlet air temperature of 165° C. The spray solution was heated to 78° C. before atomization, and the atomization to fine droplets took place using a single fluid nozzle (diameter 0.4 mm) with a pressure of 20 MPa. The outlet air temperature was 79° C.

A fine powder with an average particle size of 13 µm and an apparent density of 0.09 g/ml was obtained.

Examination under the microscope showed the presence of hollow spheres and fragments of hollow spheres (shells) with wall thicknesses of 0.8 µm.

Example 6

A 10% strength aqueous solution of a copolymer of N-vinylpyrrolidone and N-vinylcaprolactam in the ratio 1:1 by weight (K value 65, measured on a 1% by weight solution in water) was dried in a spray dryer at an inlet air temperature of 170° C. The spray solution was heated to 80° C. before the atomization, and the atomization to fine droplets took place using a single fluid nozzle (diameter 0.4 mm) with a pressure of 18.5 MPa. The outlet air temperature was 83° C.

A fine powder with an average particle size of 19 µm and an apparent density of 0.12 g/ml was obtained.

Examination under the microscope showed the presence of hollow spheres and fragments of hollow spheres (shells) with a wall thickness of 1.4 µm.

Example 7

A 12% by weight aqueous solution of a copolymer of vinylpyrrolidone and vinyl laurate (average molecular weight 20 000 dalton, K value 19) in the ratio 90:10 by weight was dried in a spray dryer at an inlet air temperature of 160° C. The spray solution was heated to 90° C. before the atomization, and the atomization to fine droplets took place using a single fluid nozzle (diameter 0.5 mm) with a pressure of 16 MPa. The outlet air temperature was 77° C.

A fine powder with an average particle size of 16 μm and an apparent density of 0.11 g/ml was obtained.

Examination under the microscope showed the presence of hollow spheres and fragments of hollow spheres (shells) with a wall thickness of 1.0 μm.

Example 8

A solution of 10% Kollidon VA 64 and 0.25% Cremophor RH 40 (product of the reaction of hydrogenated castor oil with 45 mol of ethylene oxide) in water was prepared and dried in a spray dryer at an inlet air temperature of 165° C. The spray solution was heated to 78° C. before the atomization, and the atomization to fine droplets took place using a single fluid nozzle (diameter 0.4 mm) with a pressure of 20 MPa. The outlet air temperature was 79° C.

A fine powder with an average particle size of 13 μm and an apparent density of 0.10 g/ml was obtained.

Examination under the microscope showed the presence of hollow spheres and fragments of hollow spheres (shells) with a wall thickness of 1.0 μm.

Example 9

Testing of the Effect of Binders in an Ascorbic Acid Formulation 2.00 kg of ascorbic acid, 2.31 kg of Ludipress® (coprocessed product of 93.0% lactose, 3.5% povidone and 3.5% crospovidone), 0.50 kg of binder, 0.15 kg of crospovidone (Kollidon CL, BASF), 0.0125 kg of colloidal silica (Aerosil 200, Degussa) and 0.025 kg of magnesium stearate were passed through a 0.8 mm sieve into a Turbula mixer and mixed for 10 min. This mixture was compressed in an instrumented eccentric press (EKO, from Korsch) to biplanar tablets with a diameter of 12 mm and a total weight of 500 mg. The compressive force was 18 kN.

The following binders were tested:
Product from Example 2
Product from Example 5
Product from Example 8
Kollidon VA 64 BASF commercial product, average particle size 54 μm, apparent density 0.26 g/ml
Plasdone S 630 (6.4 VPNAc copolymer) ISP commercial product, average particle size 64 μm, apparent density 0.23 g/ml
Ground Kollidon VA 64 BASF commercial product, average particle size 18 μm

| Binder | Angle of repose (°) | Resistance to crushing (N) | Ejection force (N) |
|---|---|---|---|
| No binder | 38.8 | 50 | 610 |
| Example 2 | 34.4 | 146 | 290 |
| Example 5 | 34.0 | 182 | 310 |
| Example 8 | 34.8 | 165 | 260 |
| Kollidon 64 commercial product | 37.1 | 96 | 850 |
| Plasdone S 630 commercial product | 37.3 | 94 | 910 |
| Ground Kollidon VA 64 | 36.1 | 112 | 820 |

Example 10

Testing of the Effect of Binders in a Paracetamol Formulation 2.5 kg of paracetamol, 0.655 kg of microcrystalline cellulose, 0.225 kg of binder, 0.105 kg of crospovidone (Kollidon CL, BASF), 0.025 kg of colloidal silica (Aerosil 200) and 0.015 kg of magnesium stearate were passed through a 0.8 mm sieve and mixed in a Turbula mixer for 20 min. The mixture was then compressed in a rotary tablet press (Korsch PH 106) to tablets with a diameter of 16 mm and a total weight of 705 mg. The compressive force was 10 kN.

The following binders were tested:
Product from Example 2
Kollidon VA 64 BASF commercial product, average particle size 54 μm

| Binder | Resistance to crushing (N) | Friability (%) | Disintegration (sec.) |
|---|---|---|---|
| Example 2 | 94 | 0.4 | 9 |
| Kollidon 64 commercial product | 56 | 2.0 | 12 |

Example 11

Testing of the Effect of Binders in an Ibuprofen Formulation 4.0 kg of ibuprofen, 0.3 kg of microcrystalline cellulose, 0.3 kg of binder, 0.2 kg of crospovidone (Kollidon CL, BASF), 0.06 kg of colloidal silica (Aerosil 200) and 0.03 kg of magnesium stearate were passed through a 0.8 mm sieve and mixed in a Diosna mixer for 10 min. The mixture was then compressed in a rotary tablet press (Korsch PH 106) to tablets with a diameter of 12 mm and a total weight of 489 mg. The compressive force was 9 kN.

The following binders were tested:
Product from Example 5
Kollidon VA 64 BASF commercial product, average particle size 57 μm

| Binder | Resistance to crushing (N) | Friability (%) | Disintegration (min.) |
|---|---|---|---|
| Example 5 | 92 | <0.1 | 9 |
| Kollidon 64 commercial product | 63 | 0.4 | 13 |

Example 12

An 18% strength aqueous solution of polyvinylcaprolactam (K value 23.5, 5% strength in ethanol) was dried in a spray dryer at an inlet air temperature of 135° C. The atomization to fine droplets took place using dual fluid nozzles (diameters: liquid feed 3 mm, annular gap for gas 1 mm) with a gas pressure of 0.4 MPa. The outlet air temperature was 74° C.

A fine powder with an average particle size of 15 μm and an apparent density of 0.10 g/ml was obtained.

Examination under the microscope showed the presence of hollow spheres and fragments of hollow spheres (shells) with wall thicknesses of 1.1 μm.

Example 13

A 30% strength aqueous solution of Kollidon VA 64 was dried in a spray dryer at an inlet air temperature of 153° C. The spray solution was heated to 87° C. before the atomization, and the atomization to fine droplets took place using dual fluid nozzles (diameters: liquid feed 2 mm, annular gap for gas 1 mm) with a gas pressure of 0.6 MPa. The outlet air temperature was 83° C.

A fine powder with an average particle size of 15 μm and an apparent density of 0.12 g/ml was obtained.

Examination under the microscope showed the presence of hollow spheres and fragments of hollow spheres (shells) with wall thicknesses of 1.5 μm.

We claim:

1. A finely divided binder in powder form consisting of vinyllactam polymers, where the binder has an average particle size of 2 μm to 35 μm and an apparent density of less than 0.2 g/ml, and where the binder is a tablet binder, and where the vinyllactam polymer is obtained from vinylpyrrolidone and vinyl acetate in a ratio of between 40:60 and 80:20 by weight.

2. A finely divided binder in powder form consisting of vinyllactam polymers, where the binder has an average particle size of 2 μm to 35 μm and an apparent density of less than 0.2 g/ml, and where the binder is a tablet binder, and where the vinyllactam polymer is obtained from vinylpyrrolidone and vinyl acetate in a ratio of between 50:50 and 70:30 by weight.

3. A finely divided binder in powder form consisting of vinyllactam polymers, where the binder has an average particle size of 2 μm to 35 μm and an apparent density of less than 0.2 g/ml, and where the binder is a tablet binder, and where the vinyllactam polymer is obtained from vinylpyrrolidone and vinyl acetate in a ratio of 60:40 by weight.

* * * * *